(12) United States Patent
Cheng et al.

(10) Patent No.: US 10,047,349 B2
(45) Date of Patent: Aug. 14, 2018

(54) DNA POLYMERASE POSSESSING CONTINUOUS CATALYTIC CAPACITY AND SALT TOLERANCE

(71) Applicant: Hangzhou Zhongce Bio-Sci&Tech. Co. Ltd., Hangzhou (CN)

(72) Inventors: Qi Cheng, Beijing (CN); Bing Zhai, Beijing (CN); Joseph Chow, Beijing (CN); Xianzhen Li, Beijing (CN); Guoxian Liu, Beijing (CN)

(73) Assignee: HANGZHOU ZHONGCE BIO-SCI&TECH. CO., LTD., Hangzhou (CN)

( * ) Notice: Subject to any disclaimer, the term of this patent is extended or adjusted under 35 U.S.C. 154(b) by 0 days.

(21) Appl. No.: 15/256,732

(22) Filed: Sep. 5, 2016

(65) Prior Publication Data

US 2016/0369249 A1    Dec. 22, 2016

Related U.S. Application Data

(63) Continuation-in-part of application No. PCT/CN2014/000285, filed on Mar. 17, 2014.

(30) Foreign Application Priority Data

Mar. 6, 2014 (CN) .......................... 2014 1 0079508

(51) Int. Cl.
    *C12N 9/12* (2006.01)
    *C12P 21/00* (2006.01)
    *C12N 15/70* (2006.01)

(52) U.S. Cl.
    CPC ............. *C12N 9/1252* (2013.01); *C12N 9/12* (2013.01); *C12N 15/70* (2013.01); *C12P 21/00* (2013.01); *C12Y 207/07007* (2013.01)

(58) Field of Classification Search
    None
    See application file for complete search history.

(56) References Cited

U.S. PATENT DOCUMENTS

| | | | | |
|---|---|---|---|---|
| 5,972,603 A | * | 10/1999 | Bedford et al. | ..... C12N 9/1252 435/5 |
| 2005/0026189 A1 | * | 2/2005 | Wang | ..................... G06F 19/18 435/5 |

FOREIGN PATENT DOCUMENTS

| | | |
|---|---|---|
| CN | 1676600 A | 10/2005 |
| CN | 101054569 A | 10/2007 |
| CN | 103421777 A | 12/2013 |
| WO | 9729209 A1 | 8/1997 |
| WO | 2012020015 A1 | 2/2012 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
DNA polymerase I [*Staphylococcus aureus*], Accession: WP_001038316, May 27, 2013, NCBI, United States, [online], <URL: https://www.ncbi.nlm.nih.gov/protein/446961060/>.
E. Bedford et al., The thioredoxin binding domain of bacteriophage T7 DNA polymerase confers processivity on *Escherichia coli* DNA polymerase I, Proceedings of the National Academy of Sciences, Jan. 1997, pp. 479-484, vol. 94, National Academy of Sciences, United States.
B. Lv et al., Recombinase-aid amplification: a novel technology of in vitro rapid nucleic acid amplification, Scientia Sinica Vitae, 2010, pp. 983-988, vol. 40, No. 10, Science China Press, China.

* cited by examiner

*Primary Examiner* — Richard G Hutson
(74) *Attorney, Agent, or Firm* — Swanson & Bratschun, L.L.C.

(57) ABSTRACT

A DNA polymerase, having an amino acid sequence represented by SEQ ID No. 2, or a derivative of the amino acid sequence by substitution, deletion, or addition of at least one amino acid residue. The DNA polymerase is a hybrid DNA polymerase prepared by inserting a thioredoxin binding domain (TBD) of bacteriophage T7 DNA polymerase into a DNA polymerase I (Sau) of *Staphylococcus aureus*. A method for preparing the DNA polymerase includes: 1) determining a corresponding position and a target substitution sequence in Sau protein for the TBD of the bacteriophage T7 DNA polymerase; 2) devising and synthesizing a primer according to a gene sequence of Sau and a sequence TBD published by GenBank; 3) cloning the Sau-TBD segment acquired in (2) to an expression vector pTrc99A to construct a recombinant vector pTrc99A-Sau-TBD; and 4) transforming *Escherichia coli* by the recombinant vector pTrc99A-Sau-TBD and inducing protein expression.

4 Claims, 5 Drawing Sheets

FIG. 1

```
                  222                              252
Sau DNA pol       EKLDVLIRNIHDAAGEDFNINSPKQLGVVLF
Sau-TBD DNA pol   EKLDVLIRNIHDAAG       SPKQLGVVLF
```

SWYQPKGGTEMPCHPRTGKPLPKYPRIKTPKVGGIFKK
PKNKAQREGREPCELDTREYVAGAPYTPVEHVVFNPS

DNA POLYMERASE POSSESSING CONTINUOUS CATALYTIC CAPACITY AND SALT TOLERANCE

CROSS-REFERENCE TO RELATED APPLICATIONS

This application is a continuation-in-part of International Patent Application No. PCT/CN2014/000285 with an international filing date of Mar. 17, 2014, designating the United States, now pending, and further claims priority benefits to Chinese Patent Application No. 201410079508.5 filed Mar. 6, 2014. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a DNA polymerase possessing continuous catalytic capacity and salt tolerance.

Description of the Related Art

The DNA polymerase used in the recombinase-mediated isothermal nucleic acid amplification belongs to the DNA polymerase I family. However, the DNA polymerase I family often has relatively low continuous catalytic capacity, which means that the polymerization reactions catalyzed by each binding between the polymerase and a template have low efficiency.

SUMMARY OF THE INVENTION

In view of the above-described problem, it is one objective of the invention to provide a DNA polymerase possessing continuous catalytic capacity and salt tolerance, which is a hybrid DNA polymerase prepared by inserting a thioredoxin binding domain (TBD) of bacteriophage T7 DNA polymerase into a DNA polymerase I (Sau) of S. aureus, so as to overcome the relatively low continuous catalytic capacity of the DNA polymerases of the DNA polymerase I family.

It is another objective of the invention to provide a gene encoding the DNA polymerase possessing continuous catalytic capacity and salt tolerance.

It is still another objective of the invention to provide a method for preparing the DNA polymerase possessing continuous catalytic capacity and salt tolerance.

It is still another objective of the invention to provide a method for using the DNA polymerase possessing continuous catalytic capacity and salt tolerance.

To achieve the above objective, in accordance with one embodiment of the invention, there is provided a DNA polymerase possessing continuous catalytic capacity and salt tolerance, being a hybrid DNA polymerase prepared by inserting a thioredoxin binding domain (TBD) of bacteriophage T7 DNA polymerase into a DNA polymerase I (Sau) of S. aureus, having an amino acid sequence represented by SEQ ID No. 2 or an amino acid sequence of similar functions by substitution, deletion, or addition of at least one amino acid residue.

In accordance with another embodiment of the invention, there is provided a gene encoding the DNA polymerase possessing continuous catalytic capacity and salt tolerance, having a nucleotide sequence represented by SEQ ID No. 1.

In accordance with still another embodiment of the invention, there is provided a method for preparing the DNA polymerase possessing continuous catalytic capacity and salt tolerance. The method comprises:

1) determining a corresponding position and a target substitution sequence in Sau protein for the TBD of the bacteriophage T7 DNA polymerase;
2) devising and synthesizing a primer according to a gene sequence of Sau and a sequence TBD published by GenBank, and amplifying by Overlap PCR to insert the TBD into the corresponding position of the gene sequence of Sau to prepare a Sau-TBD segment having a purification tag and a restriction site;
3) cloning the Sau-TBD segment obtained in (2) to an expression vector pTrc99A to construct a recombinant vector pTrc99A-Sau-TBD; and
4) transforming E. coli by the recombinant vector pTrc99A-Sau-TBD and inducing protein expression.

In accordance with still another embodiment of the invention, there is provided a method for using the DNA polymerase possessing continuous catalytic capacity and salt tolerance in isothermal nucleic acid amplification.

Advantages of the DNA polymerase possessing continuous catalytic capacity and salt tolerance according to embodiments of the invention are summarized as follows:

The DNA polymerase used in the isothermal nucleic acid amplification is biomolecularly constructed. The DNA polymerase after construction maintains the same catalytic activity as the original, but the continuous catalytic capacity thereof is significantly improved and the salt tolerance thereof in the recombinase-mediated isothermal nucleic acid amplification reaction is also improved. When conducting the nucleic acid detection in the field or the site, because the simple DNA extraction technique is employed, DNA samples prepared are usually not pure enough and may contain amplification inhibiting substances like salt ions. The DNA polymerase after construction has much higher salt tolerance and is capable of significantly improving the DNA amplification effect of the recombinase-mediated isothermal nucleic acid amplification in the field or the site, thus having wide application prospect.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a DNA polymerase possessing continuous catalytic capacity and salt tolerance are described below. It should be noted that the following examples are intended to describe and not to limit the invention.

Source of biomaterials of the invention:

1. *S. aureus* CICC21600 was purchased from China Center of Industrial Culture Collection (CICC), and *E. coli* BL21 (DE3) was purchased from Novagen company.

2. Primers and plasmid pUC57-TBD containing the TBD gene was authorized to BGI Biological Technology Co., Ltd for synthesis.

3. Vectors pTrc-99A and pET28a were purchased from Novagen company.

Example 1

Figure 1:
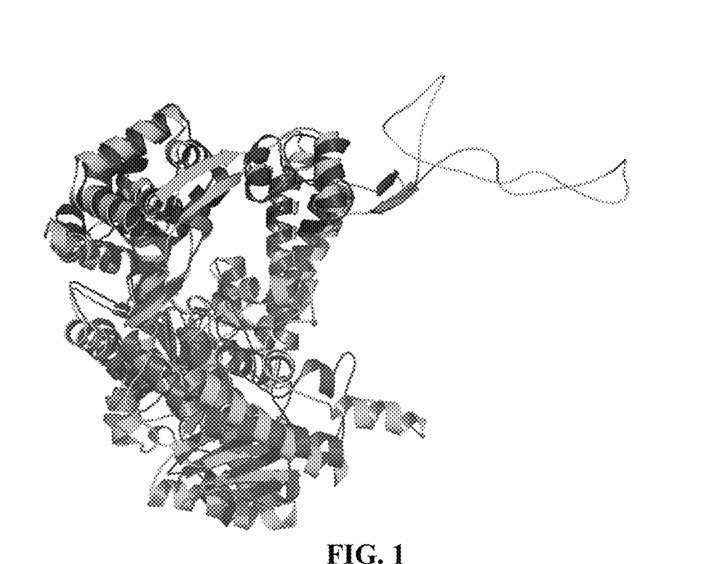
FIG. 1 illustrates three-dimensional structure prediction and overlapping match results of bacteriophage T7 DNA polymerase and Sau protein.
Figure 2:
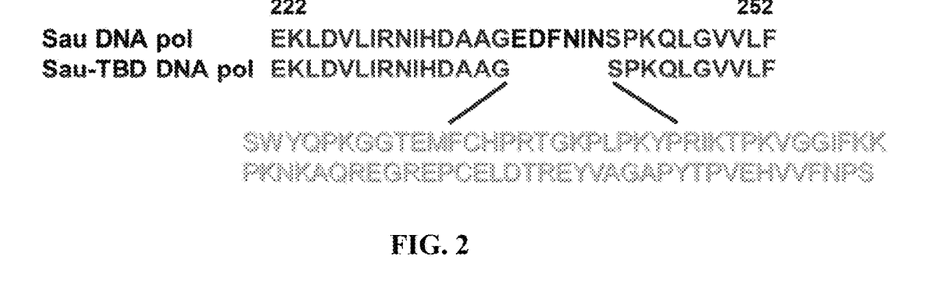
FIG. 2 shows insertion position of TBD domain into Sau protein sequence.
Figure 3:
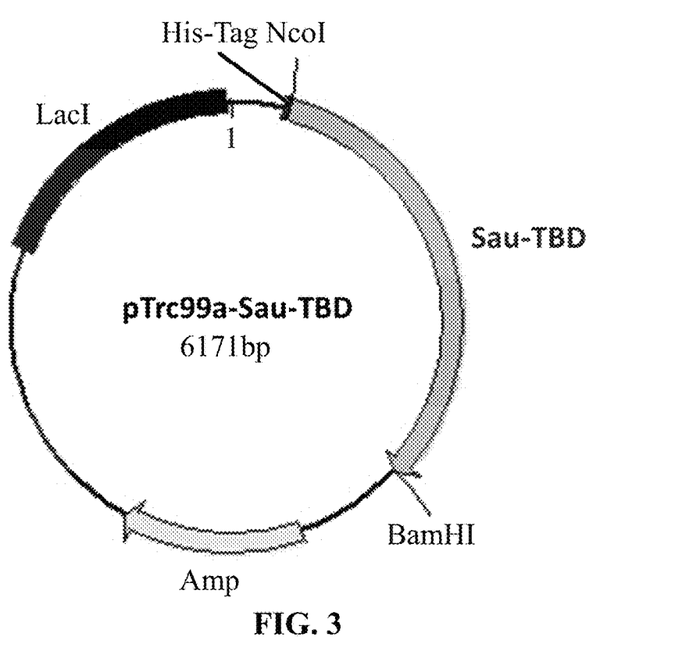
FIG. 3 illustrates construction of a recombinant plasmid of pTrc99A-Sau-TBD.

Three-dimensional structures of the bacteriophage T7 DNA polymerase and the Sau were predicted on swissmodel website (http://swissmodel.expasy.org/) according to the sequence information disclosed by GenBank. Thereafter, the three dimensional structures of the bacteriophage T7 DNA polymerase (PDB: 2AJQ_A) and the Sau (PDB: 4DQQ_D) were compared using the DaliLite function on EBI website (http://www.ebi.ac.uk/Tools/structure/dalilite/) so as to find the position in the Sau protein sequence corresponding to the TBD and determine the substitution sequence (as shown in FIGS. 1-2).

Example 2

Preparation of the Sau-TBD segment is illustrated hereinbelow.

1. The sequence of the TBD (registration number in NCBI is ACY75853.1, and sequence is represented by SEQ ID No. 3) of the bacteriophage T7 DNA polymerase was synthesized according to the GenBank and related literatures.

2. Primers were devised and synthesized according to the gene sequence of Sau (reference sequence number in NCBI is YP_006237943.1) and the sequence information of TBD disclosed by GenBank.

PT1_F:
(SEQ ID No. 4)
5'-CATGCCATGGAACATCATCATCATCATCATTCAGCAAGCGTTGAAG-3' (NcoI)

PT1_R:
(SEQ ID No. 5)
5'-GATACCACGA ACCAGCTGCATCATGGAT-3'

PT2_F:
(SEQ ID No. 6)
5'-GTTGTGTTTAACCCTTCGTCTCCTAAGCAATTAGGTG-3'

PT2_R:
(SEQ ID No. 7)
5'-CGCGGATCCTTATTTTGCATCATACC-3' (BamHI)

TBD_F:
(SEQ ID No. 8)
5'-TGCAGCTGGTTCGTGGTATCAGCCTAAAGG-3'

TBD_R:
(SEQ ID No. 9)
5'-CACCTAATTGCTTAGGAGACGAAGGGTTAAACACAAC-3'

3. PT1_F/PT1_R and PT2_F/PT2_R were used as specific primers and genosome of *S. aureus* CICC21600 was used as the template to perform PCR amplification respectively. The specific primer TBD_F/TBD_R was adopted as the specific primer, and the artificially synthesized plasmid pUC57-TBD containing the TBD gene was used as the template for performing PCR amplification. PCR reaction system is a common amplification system recommended by PrimeSTAR HS (TAKARA), and the PCR reaction program was as follows: predenaturation at 98° C. for 2 min, followed by 27 cycles of denaturation at 98° C. for 10 s, annealing at 55° C. for 30 s, and extension at 72° C. for 1 min, and finally followed by extension at 72° C. for 10 min. Reaction products were preserved at 4° C.

4. PT1, PT2, TBD segments were recovered using a gel extraction kit for PCR products as follows:

1) An agarose gel containing a target segment was cut using a surgical blade under an ultraviolet light and placed in a 1.5 mL centrifuge tube.

2) An extraction buffer was added to the centrifuge tube according to a ratio of 1:3 to yield a mixed solution.

3) The centrifuge tube was then placed in a water bath at a constant temperature of 50° C. for 10 min, during which the centrifuge tube was gently reversed every two minutes.

4) The mixed solution was transferred to a spin column and the spin column was centrifuged at a rotational speed of 6000×g for 1 min. A solution in a collection tube was discarded.

5) 500 µL of the extraction buffer was added to the spin column which was then centrifuged at a rotational speed of 12 000×g for 1 min, and a solution in a liquid collection tube was discarded.

6) 750 µL of a wash buffer was added to the spin column which was then centrifuged at the rotational speed of 12 000×g for 1 min, and a solution in the liquid collection tube was discarded.

7) The spin column was placed into the collection tube and centrifuged at the rotational speed of 12 000×g for 1 min. The spin column was then transferred to an aseptic 1.5 mL EP tube.

8) 50 µL of an elution buffer was added to the spin column and the spin column was allowed to stand for 1 min at the room temperature. Thereafter, the spin column was centrifuged at the rotational speed of 12 000×g for 1 min so as to collect the target DNA segments in a micro centrifuge tube. The target DNA segments were preserved at a temperature of −20° C.

5. PT1 segment and TBD segment were used as templates and PT1_F and TBD_R were used as primers to perform overlap PCR. The amplification system was as follows:

| | |
|---|---|
| 10* PrimeSTAR Buffer | 10 μL |
| dNTP | 4 μL |
| PT1 | 0.2 μL |
| TBD | 0.2 μL |
| PT1_F | 2 μL |
| TBD_R | 2 μL |
| PrimeSTAR Pol | 0.5 μL |
| ddH$_2$O | 31.1 μL |

The PCR reaction program was as follows: predenaturation at 98° C. for 2 min, followed by 27 cycles of denaturation at 98° C. for 10 s, annealing at 55° C. for 30 s, and extension at 72° C. for 1 min, and finally followed by extension at 72° C. for 10 min. Reaction products were preserved at 4° C.

6. PT1-TBD segment was recovered using the gel extraction kit for PCR products.

7. PT1-TBD segment and PT2 segment were used as templates and PT1_F and PT2_R were used as primers to perform overlap PCR. The amplification system was as follows:

| | |
|---|---|
| 10* PrimeSTAR Buffer | 10 μL |
| dNTP | 4 μL |
| PT1-TBD | 0.2 μL |
| PT2 | 0.2 μL |
| PT1_F | 2 μL |
| PT2_R | 2 μL |
| PrimeSTAR Pol | 0.5 μL |
| ddH$_2$O | 31.1 μL |

The PCR reaction program was as follows: predenaturation at 98° C. for 2 min, followed by 27 cycles of denaturation at 98° C. for 10 s, annealing at 58° C. for 30 s, and extension at 72° C. for 1 min, and finally followed by extension at 72° C. for 10 min. Reaction products were preserved at 4° C.

8. The PT1-TBD-PT2 (Sau-TBD) segment was recovered by gel extraction kit for PCR products.

Example 3

Construction of recombinant plasmid pTrc99A-Sau-TBD is illustrated hereinbelow:

1. Sau-TBD segment and vector pTrc99A were digested by enzyme at 37° C. for 2 hrs and the digestion products were recovered by gel extraction. The enzyme digestion system was as follows:

| | |
|---|---|
| 10 × NEB Buf 3 | 5 μL |
| NcoI | 1 μL |
| BamHI | 1 μL |
| BSA | 0.5 μL |
| Sau-TBD/pTrc99A | 42.5 μL |

2. Sau-TBD and pTrc99A segments after digestion were ligated by a T4 ligase overnight at 16° C. using the following ligation system:

| | |
|---|---|
| 10 × Ligase Buf | 2.5 μL |
| T4 ligase | 1 μL |
| Sau-TBD | 8 μL |
| pTrc99A | 8.5 μL |

3. Transformation: competent cells of *E. coli* DH5α were taken out from −70° C. refrigerator and buried in ice. Ligation products were taken out from a water bath at the temperature of 16° C., removed from a sealing film, and placed on the ice. When the competent cells were melted, the ligation products were added to 100 μL of the competent cells of DH5a and uniformly mixed. After 30 min treatment by the ice, the mixture was heated at 42° C. for 90 s, and then treated by the ice again. Then 800 μL of an LB culture medium was added to the mixture, a resulting mixture was shaken on a shaking table at a rotational speed of 170 rpm at the temperature of 37° C. for 1 hr. A culture was then centrifuged at a rotational speed of 5 000 rpm for 5 min. A part of supernatant was discarded to leave approximately 100 μL of the remaining. The remaining supernatant and a precipitant were mixed and a resulting mixture was then smeared on a Kanamycin resistant LB plate and incubated at 37° C. for between 12 and 16 hrs.

4. A plurality of pTrc99A-Sau-TBD colonies were picked and cultured on a shaking table at the temperature of 37° C. overnight, then an amount of plasmid DNA was extracted as follows:

1) 2 mL of a fresh bacterial liquid was collected and centrifuged at the rotational speed of 12 000×g for 1 min, and a supernatant was then discarded, leaving a bacterial precipitate.

2) 250 μL of Buffer S1 was added to suspend the bacterial precipitate. A suspension was required to be uniform to avoid bacterial mass.

3) 250 μL of Buffer S2 was added to the suspension, a resulting solution was gently and fully reversed for between 4 and 6 times to make bacteria totally decomposed.

4) 350 μL of Buffer S3 was added, a resulting mixture was fully reversed for mixing for between 6 and 8 times, and then centrifuged at the rotational speed of 12 000×g for 10 min.

5) A supernatant was sucked and transferred to a preparation tube which was then centrifuged at the rotational speed of 12 000×g for 1 min. A filtrate was then discarded.

6) 500 μL of a Buffer W1 was added to the preparation tube which was then centrifuged at the rotational speed of 12 000×g for 1 min. A filtrate was then discarded.

7) The preparation tube was put back in the collection tube, added with 700 μL of a Buffer W2, and centrifuged at the rotational speed of 12 000×g for 1 min, then a filtrate was discarded.

8) The preparation tube was centrifuged at the rotational speed of 12 000×g for 1 min.

9) The preparation tube was then transferred to a new 1.5 mL centrifuge tube, and 70 μL of an Eluent was added to the preparation tube. The preparation tube was allowed to stand at the room temperature for 1 min, and then centrifuged at the rotational speed of 12 000×g for 1 min. Resulting products were preserved at the temperature of −20° C.

5. Identification of the recombinant plasmid

1) Identification of the recombinant plasmid by PCR

The extracted plasmid were amplified by PCR, and performed with 1% agarose gel electrophoresis to observe the results.

2) Identification of recombinant plasmid by double digestion

The double digestion system of pTrc99A-Sau-TBD was as follows:

| | |
|---|---|
| 10 × NEB Buf 3 | 5 µL |
| NcoI | 1 µL |
| BamHI | 1 µL |
| BSA | 0.5 µL |
| Sau-TBD/pTrc99A | 42.5 µL |

Figure 4:
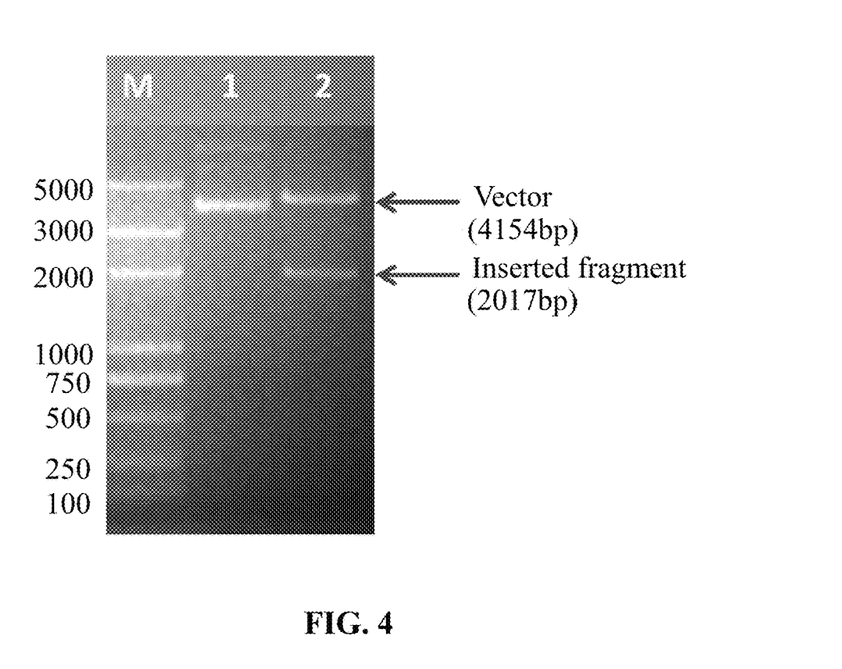
FIG. 4 shows identification results of a recombinant plasmid of pTrc99A-Sau-TBD by enzyme digestion, in which, M indicates Marker, 1 indicates a plasmid pTrc99A-Sau-TBD, 2 indicates double digestion products of the plasmid pTrc99A-Sau-TBD.

The digestion was performed at the temperature of 37° C. for 2 hrs. 1% agarose gel electrophoresis was performed to identify the results, which was shown in FIG. 4.

6. Recombinant plasmid that was identified to be correct by digestion was sent to sequence.

Example 4

The expression and purification of the recombinant protein is introduced hereinbelow:

1. Recombinant expression plasmid pTrc99A-Sau-TBD testified by sequencing to be positive was then transformed into *E. coli* expression strain BL21 (DE3). A signal colony was picked and incubated in an LB liquid culture medium containing kanamycin on a shaking table at the temperature of 37° C. overnight.

2. A bacterial liquid was inoculated to 500 mL of the LB liquid culture medium containing kanamycin according to a ratio of 1/100 and cultured on the shaking table at the temperature of 37° C. When the $OD_{600}$ reached 0.6, IPTG was added until a final concentration was 0.5 mmol/L, then the induction was performed. An expression vector contrast group was designed, a bacterial liquid was collected 4 hrs after the induction expression, centrifuged at the rotational speed of 12 000 rpm for 10 min, and a supernatant was removed.

3. Ni-NTA loading buffer (20 mM $Na_3PO_4$, 0.5 M NaCl, 10 mM imidazole, pH 7.4) was used to heavily suspend a bacteria precipitate. The bacteria precipitate was then treated with ultrasonication, centrifuged at 10 000 rpm for 20 mM. Thereafter, a supernatant and a precipitate were performed with SDS-PAGE electrophoresis.

4. AKTA protein purification system and Ni Sepharose 6 Fast Flow affinity chromatography were employed to perform affinity purification of the target protein, in which the loading buffer (20 mM $Na_3PO_4$, 0.5 M NaCl, 10 mM imidazole, pH 7.4) and the elution buffer (20 mM $Na_3PO_4$, 0.5 M NaCl, 500 mM imidazole, pH 7.4) were adopted. Protein sample at an elution peak was collected and treated by dialysis (10 mM Tris-HCl pH 7.5, 50 mM KCl, 1 mM DTT, 1 mM EDTA, 0.1% NP-40) overnight at the temperature of 4° C.

Figure 5:
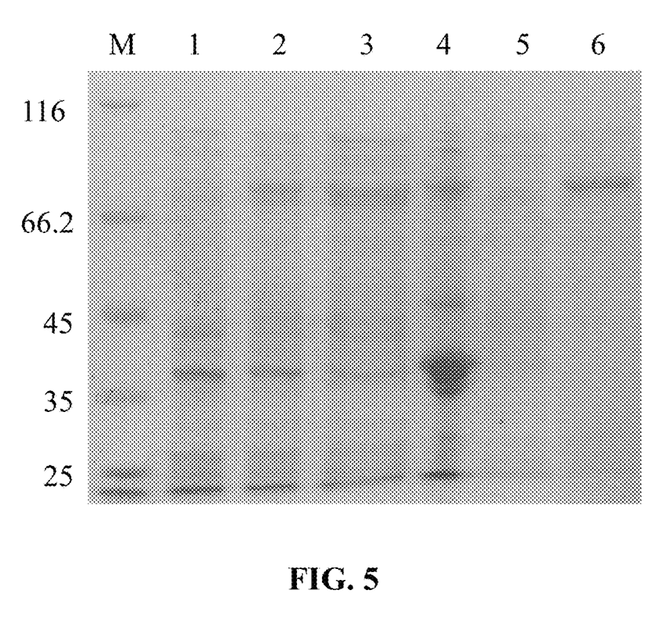
FIG. 5 is SDS-PAGE analysis results of a recombinant protein Sau-TBD, in which, M indicates Marker, 1 indicates a protein before induction, 2 indicates a protein after induction, 3 indicates a supernatant, 4 indicates a precipitate, 5 indicates a flow solution, and 6 indicates a target protein (approximately 73 KD)

5. AKTA protein purification system and HiTrap Heparin HP affinity chromatography were employed to perform a secondary purification on the protein sample after dialysis overnight, in which the loading buffer (10 mM $Na_3PO_4$, pH 7.0) and the elution buffer (10 mM $Na_3PO_4$, 1 M NaCl, pH 7.0) were adopted. Protein sample at an elution peak was collected and treated by dialysis (10 mM Tris-HCl pH 7.5, 50 mM KCl, 1 mM DTT, 1 mM EDTA, 0.1% NP-40) overnight at the temperature of 4° C. The protein samples after the dialysis was preserved at the refrigerator at the temperature of −80° C. Electrophoresis results of protein samples at different phases of the purification process were shown in FIG. 5.

Comparative Example 1

Because TrxA was necessary herein, a premier was devised and synthesized according to the gene sequence of TrxA disclosed by GenBank (reference sequence number in NCBI is NC_000913.2) so as to prepare the protein:

```
Trx_F:
                                    (SEQ ID No. 10)
5'-CATGCCATGGGCAGCGATAAAATTATTCACCTG-3'  (NcoI)

Trx_R:
                                    (SEQ ID No. 11)
5'-TTTTCCTTTTGCGGCCGCCGCCAGGTTAGCGTCGAGG-3'
(NotI)
```

Figure 6:
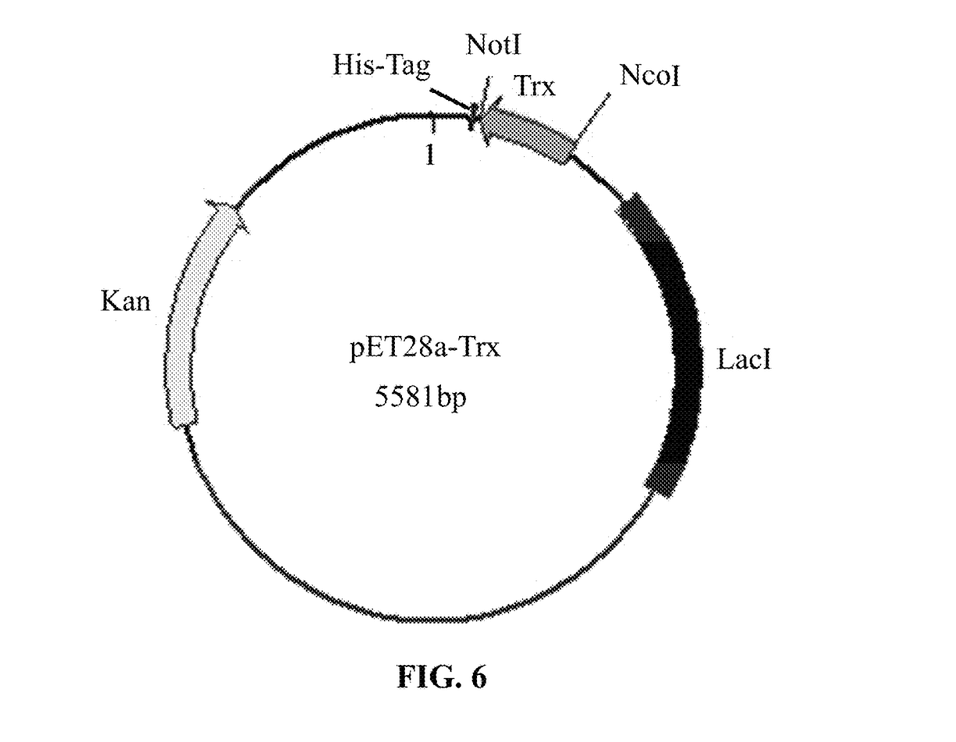
FIG. 6 is a diagram showing construction of recombinant plasmid pET28a-Trx.
Figure 7:
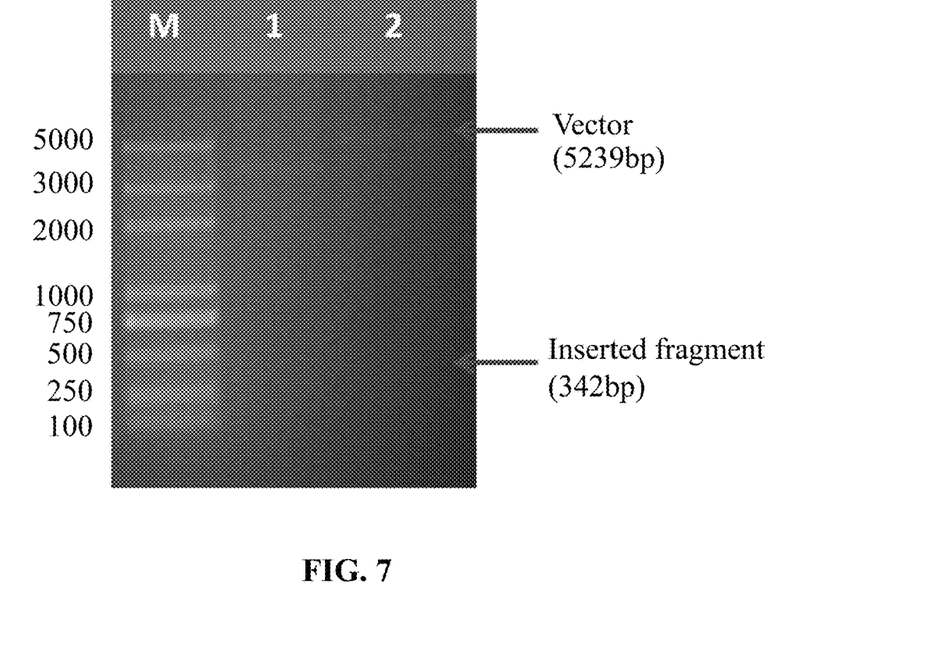
FIG. 7 shows identification results of a recombinant plasmid of pET28a-Trx by enzyme digestion, in which, M indicates Marker, 1 indicates a plasmid pET28a-Trx, 2 indicates double digestion products of the plasmid pET28a-Trx.
Figure 8:
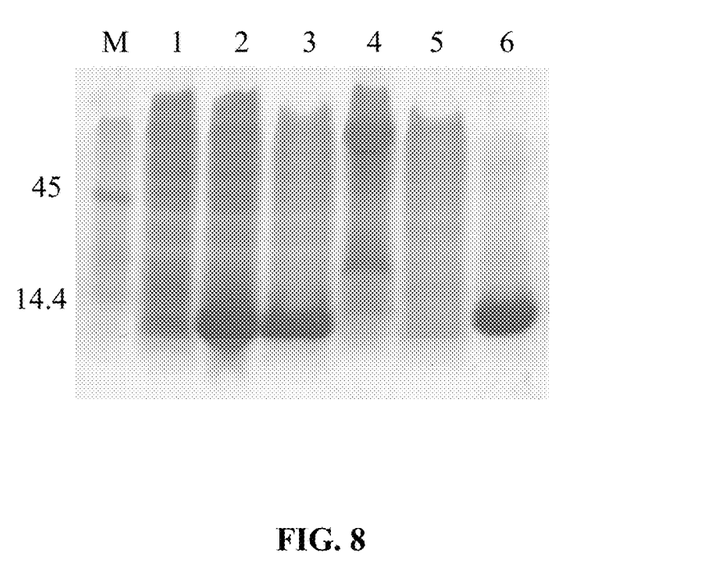
FIG. 8 shows SDS-PAGE analysis results of a recombinant protein Trx, in which, M indicates Marker, 1 indicates a protein before induction, 2 indicates a protein after induction, 3 indicates a supernatant, 4 indicates a precipitate, 5 indicates a flow solution, and 6 indicates a target protein (approximately 13 KD)

Trx_F/Trx_R were used as specific premiers and genome of *E. coli* BL21 (DE3) was used at the template to perform PCR amplification. The amplified segments were then recovered and ligated to pET28a, followed by transformation, expression, and SDS-PAGE electrophoresis. All experiment methods are common operations, which can refer to Examples 2-4, and results thereof are shown in FIGS. 6-8.

Hereinbelow, the polymerization activities were compared between the polymerase Sau before the protein construction and the polymerase Sau-TBD after the protein construction:

1. Test reaction: the synthesized premier M13-40 and ssM13mp18 DNA (NEB) were annealed in the standard recombinase-mediated isothermal nucleic acid amplification reaction system, then 300 µM of dNTPs and 1.5 µM of (Sau/Sau-TBD) were respectively added. An additional 1.5 µM of TrxA was then added to the Sau-TBD reaction system. Finally, 14 mM of MgAc was added to each reaction tube to start the reaction. Amplification reaction was performed at the temperature of 37° C., and samples at different time points were collected for testing.

```
The sequence of M13-40 is:
5'-GTTTTCCCAGTCACGACG-3'    (SEQ ID No. 12)
```

2. Control reaction: the synthesized premiers M13-40 and ssM13mp18DNA (NEB) were annealed in 10× ThermoPol Buffer, then 300 µM of dNTPs and 1.5 µM of Bst (NEB) were respectively added. Amplification reaction was performed at 65° C., and samples were collected at different time points for testing.

3. An equivalent volume of PicoGreen (Invitrogen) digested at a ratio of 1:200 were added to amplification products and uniformly mixed to allow for reaction for between 2 and 5 min in the dark. Fluorescence intensities of different reaction tubes were tested by microplate reader (Fluostar Optima, BMG LABTECH).

4. The initial reaction rates of Sau and Sau-TBD were compared to the initial reaction rate of Bst, the polymerization activity of which was known, so as to obtain the polymerization activity of Sau and Sau-TBD (containing Trx), results of which were listed in Table 1.

TABLE 1

Results of polymerization activities

| Polymerase | Polymerization activities (units/mg protein) | |
| --- | --- | --- |
| | −TrxA | +TrxA |
| Sau | 3089 | 3099 |
| Sau-TBD | 1316 | 2864 |

It is known from Table 1 that the polymerization activity of Sau protein is not influenced by the addition of the TrxA. While without the assistance of the TrxA, the polymerization activity of Sau-TBD is only 1316 units/mg. Under the assistance of TrxA, the polymerization activity of Sau-TBD is improved by at least two folds and reaches 2864 units/mg. According to the difference of the molar mass, the polymerization activity per molar unit of Sau and Sau-TBD have no significant difference.

Comparative Example 2

The continuous synthetic capacities were compared between the polymerase Sau before the protein construction and the polymerase Sau-TBD after the protein construction:

1. The whole reaction was performed in the dark condition: fluorescent labeled primers M13-40LF and ssM13mp18 DNA(NEB) were annealed in the standard recombinase-mediated isothermal nucleic acid amplification reaction system, then 300 μM of dNTPs and polymerase (Sau/Sau-TBD) were respectively added. Polymerase (a ratio of the polymerase to the template after annealing of the primer was 1:100-1:2000) of different concentrations were respectively added to different reaction tubes to find the conditions of reaching continuous synthetic state for different polymerses (generally enzyme possessing high continuous catalytic capacity requires a relative high ratio of the polymerase to the template after the annealing of the primer to reach the continuous synthetic state). An additional 50 mM of TrxA was added to the Sau-TBD reaction system. Finally 14 mM of MgAc was added to each reaction tube to initiate the reaction.

Sequence of M13-40LF is as follows:

(SEQ ID No. 13)
5'-FAM-GTTTTCCCAGTCACGACGTTGTAAAACGACGGCC-3'

2. The whole reaction was performed in the dark: the amplification reaction was performed at 37° C. In order to prevent the polymerase from extending the same amplification product for multiple times, the reaction products were taken out at different time periods. When the reaction was finished, 50 mM of EDTA was added to each reaction tube to end the reaction.

3. The reaction product was diluted by the loading buffer, and the samples was load to DNA sequencer (3730xl DNA Analyzer, Applied Biosystems), and fluorescence peaks of the electrophoresis of reaction product and the length data of the corresponding amplification products were shown in FIG. 5.

4. Length data of the amplification products of Sau and Sau-TBD were analysed, and an average length of the amplified products of each polymerase was calculated according to the following equation:

$$\log(n_I/n_T) = (n-1)\log P_I + \log(1-P_I)$$

In the equation, $n_I$ represents a length of a signal peak that is higher than the background, and $n_T$ represents a sum of signal intensity of all products. A curve of $\log(n_I/n_T)$ was charted in relation to n−1, in which n represents a number of bases polymerized at an end of the primers. Thus, it was known from the equation that an average amplification length of the primer was $1/(1-P_I)$, in which $P_I$ represents a probability that the polymerization does not stop at the position of I, results were listed in Table 2.

TABLE 2

Continuous catalytic capacities of polymerases

| Polymerases | Micro continuous synthetic capacities ($P_I$) | Average amplification length of primers (nt) [$1/(1 - P_I)$] |
| --- | --- | --- |
| Sau | 0.9726 ± 0.0006 | 36.5 ± 0.8 |
| Sau-TBD (in the presence of TrxA) | 0.9865 ± 0.0001 | 74.1 ± 0.6 |
| Sau-TBD (in the absence of TrxA) | 0.7135 ± 0.004 | 3.5 ± 0.06 |

Figure 9:
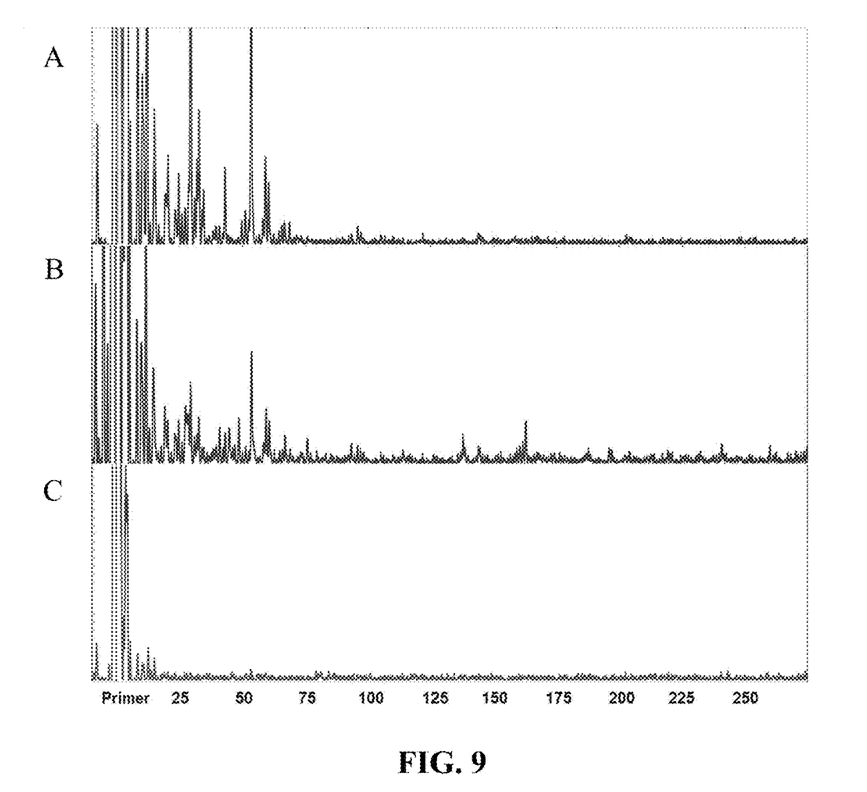
FIG. 9 shows electrophoresis peaks for testing continuous catalytic capacity of Sau and Sau-TBD, in which, an abscissa indicates an addition of nucleotides, and an ordinate indicates a fluorescence intensity.

It is known from Table 2 and FIG. 9 that the insertion of the TBD domain into the polymerase Sau make the average amplification length of the primer reduced from 36.5 nt to 3.5 nt, such decrease may because the TBD domain influences the binding effect of the Sau polymerase on the DNA chain. While under the assistance of the TrxA, the average amplification length of the primer of the Sau-TBD is significantly improved by at least 20 folds and reaches 74.1 nt, which is more than two times of the wild-type Sau polymerase. This indicates that under the binding effect of TrxA to the DNA, the continuous catalytic capacity of the Sau-TBD after construction has is significantly enhanced.

Comparative Example 3

The salt tolerances were compared between the polymerase Sau before the protein construction and the polymerase Sau-TBD after the protein construction:

1. λ phage DNA (130 pg/μL) was used as the template, and 500_F/500_R is used as the primer, and the amplification reaction was performed in the common recombinase-mediated isothermal nucleic acid amplification reaction system. KAc of different concentrations were added into different reaction tubes so as to study the tolerance of the system to the salt concentrations.

(SEQ ID No. 14)
500_F: 5'-ACTACTAAATCCTGAATAGCTTTAAGAAGG-3'

(SEQ ID No. 15)
500_R: 5'-CAGAAAGCTAAATATGGAAAACTACAATAC-3'

2. The reaction was performed at 37° C. for 40 mM. After the reaction, an equivalent volume of phenol chloroform was added to the system for extraction. 5 μL of a supernatant sample yield from the extraction was collected and performed with electrophoresis in 1.2% agarose gel, and the electrophoresis result is shown in FIG. 10.

Figure 10:
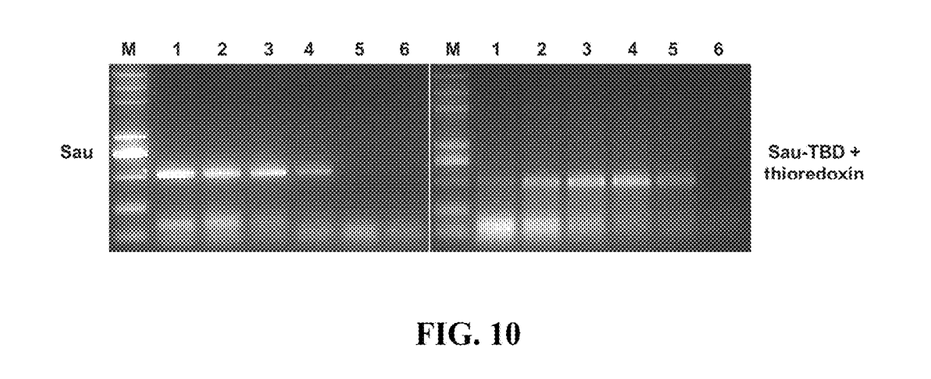
FIG. 10 shows electrophoresis results of salt tolerances of Sau and Sau-TBD.

It is indicated from the results illustrated in FIG. 10, Sau can be normally amplified in condition of relative low KAc concentration (<160 mM). When the concentration of KAc reaches 180 mM, Sau is uncapable of amplifying to yield visible band. In contrast, Sau-TBD is capable of amplifying at 180 mM under the help of TrxA to obtain clear band. It is concluded that Sau-TBD (in the presence of TrxA) has much higher salt tolerance in the recombinase-mediated isothermal nucleic acid amplification system, thus, it has significant advantage in the amplification process of DNA samples that have relatively higher salt.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A hybrid DNA polymerase, having the amino acid sequence of SEQ ID NO: 2, wherein the hybrid DNA polymerase is prepared by inserting a thioredoxin binding domain (TBD) of bacteriophage T7 DNA polymerase into a DNA polymerase I (Sau) of *Staphylococcus aureus*.

2. A polynucleotide encoding the DNA polymerase of claim 1, having the nucleotide sequence of SEQ ID NO: 1.

3. A method for preparing the DNA polymerase of claim 1, comprising:
   1) determining a corresponding position and a target substitution sequence in Sau protein for the TBD of the bacteriophage T7 DNA polymerase;
   2) devising and synthesizing a primer according to the gene sequence of Sau and the sequence TBD and amplifying by overlap PCR to insert the TBD into the corresponding position of the gene sequence of Sau to prepare a Sau-TBD segment having a purification tag and a restriction site;
   3) cloning the Sau-TBD segment obtained in (2) into an expression vector pTrc99A to construct a recombinant vector pTrc99A-Sau-TBD; and
   4) transforming *Escherichia coli* with the recombinant vector pTrc99A-Sau-TBD and inducing protein expression.

4. A method for isothermal nucleic acid amplification comprising adding the DNA polymerase of claim 1 to a reaction mixture comprising a target nucleic acid sequence, primers and nucleotides and performing DNA amplification.

* * * * *

SEQUENCE LISTING

```
<160> NUMBER OF SEQ ID NOS: 15

<210> SEQ ID NO 1
<211> LENGTH: 2838
<212> TYPE: DNA
<213> ORGANISM: Artificial Sequence
<220> FEATURE:
<223> OTHER INFORMATION: gene  fragment of Sau-TBD

<400> SEQUENCE: 1
gtgaataaat tagtattaat cgatggtaat agcttaagtt ttagagcttt ttatgcatta      60
cctttgttat caaacaaagc aggcattcat accaatgcag tatatggttt tgcaatgtta     120
ctagagaaga ttttaaaaga agaaaagcca aatcattttt tagtagcgtt tgatgcaggt     180
aaaacgactt tcagacatga aaaatatagt gaatataaag gtggacgcca gaaaacgccg     240
cctgaactaa gtgagcaatt tccttatata cgccaattat tagatgcata tcatattaaa     300
cgttatgaat tagataacta tgaggcagat gatattatcg gaactttaag taagaagca     360 gataaagcgg gctttcagac aattattatt acgggagacc gagatttaac acaacttgca     420
acggataatg taaccattta ttacactaaa aaaggtgtta ctgatgttga tcattataca     480
cctgacttta ttgcggaaaa atacaacggg ttaacaccta atcaaattat tgatatgaaa     540
ggattaatgg gagatacttc tgataatata ccaggtgttg caggtgttgg agagaaaaca     600
gcaataaaat tgctaaacca atttgacaca gtagaaggtg tctatgaaca tttagatgaa     660
atttcaggta aaagttaaa agagaaactt caaaatagca aagaagatgc attaatgagt     720
aaagaattag caacgattaa tgtagatagt ccgattgaag taaaacttga agatacgtta     780
atgactcatc aagatgaaca acaagaaaaa atcgaattgt ttaagaagtt agaattcaaa     840
caattgttgg ctgacattga tcaatcagca agcgttgaag atgcaataga aaagacaatt     900
gaaattgaaa cgtctttga taatgttgat tttacttcat tgaaagaagc ggccatccat     960
ttcgaattag acggtggtaa ctatttgcga aataatattt taaaattctc tttatttaca    1020
ggtgagaaac atattgtaat taatgcggat gacataaata attatgccga actagtttca    1080
tggttagaaa atccgaatac gaaaaaagtc gtatatgatg ctaaaaaaac atatgtagca    1140
tcacatagat tgggaattga tattcaaaat atttctttcg atattatgtt ggccagttat    1200
ataattgatc catctcgtac gattagtgat gttcaatcag ttgtttcatt gtacggtcaa    1260
agttttgtga aagacgatgt gagtatatat ggaaaaggta agaaatttaa ggtacctgaa    1320
gatgatgttt taaatccata tgttgcttct attactgatg caatttactt tgcgaaacca    1380
aatatggata acaattaga agaatacaat caggtagaac tcttagctga tttagagcta    1440
ccgctagcta agattttaag tgaaatggaa gaaattggta tatttacaga tgttcatgat    1500
ttagaagaaa tggaaaaaga aattcaagaa aaattagacg tcttgattcg aaatatccat    1560
gatgcagctg gttcgtggta tcagcctaaa ggtggcactg agatgttctg ccatccgcga    1620
acaggtaagc cactacctaa ataccctcgc attaagacac ctaaagttgg tggtatcttt    1680
aagaagccta agaacaaggc acagcgagaa ggccgtgagc cttgcgaact tgatacccgc    1740
gagtacgttg ctggtgctcc ttacaccccca gttgaacatg ttgtgtttaa cccttcgtct    1800
```

```
cctaagcaat taggtgttgt attgtttgag acattacaat tacctgttat taaaaagacg    1860
aaaacaggat attctactgc tgtagatgtc ttagagcaat tgcaaggtga acatcctatc    1920
attgattata ttttagaata tcgtcaatta tctaagttac agtctactta tgttgaagga    1980
ttgcaaaagg taattagtga tgatcaacgt atccatacac gttttaacca aactttagcg    2040
caaactggac gtttatcaag tgtagatcct aatttacaaa atattccggt tagacttgaa    2100
gaagggcgta aaataagaaa agcctttaaa ccaacttcaa aagatagcgt tatattatca    2160
gcagattatt ctcaaattga attgcgtgta ttagcacaca ttacacaaga tgagagtatg    2220
aaagaagcat ttatcaacgg cgatgatatt catacagcac tgctatgaa agtatttggt    2280 gtagaagctg atcaagtcga tagtttaatg cgtcgtcaag caaaagcggt taactttgga    2340
attgtttatg ggataagtga ttatggttta agtcaaagtt taggtattac tcgtaaaaaa    2400
gcaaaagcat tcattgatga ttatttagct agtttcccag gtgtaaaaca atatatgtct    2460
gatattgtaa aagatgccaa agctttaggt tatgtggaaa cattgctaca tcgtcgacgc    2520
tatattcctg atattacgag tcgtaacttt aatttacgcg gctttgctga acgtactgct    2580
atgaatacgc caatacaagg cagtgctgca gatatcatta aactggcaat ggttaaattt    2640
gcacaaaaaa tgaaagagac aacatatcaa gctaaactat tattacaagt acacgatgaa    2700
ttaatttttg aagtacctaa gtcagaagta gattcattta gtgaatttgt agaagagata    2760
atggaaaatg cattgcaatt agatgttcca ttaaaagtag actcaagtta tggtgcaact    2820
tggtatgatg caaaataa                                                  2838

<210> SEQ ID NO 2
<211> LENGTH: 945
<212> TYPE: PRT
<213> ORGANISM: Artificial Sequence
<220> FEATURE:
<223> OTHER INFORMATION: amino acid sequence encoded by gene Sau-TBD

<400> SEQUENCE: 2

Val Asn Lys Leu Val Leu Ile Asp Gly Asn Ser Leu Ser Phe Arg Ala
1               5                   10                  15

Phe Tyr Ala Leu Pro Leu Leu Ser Asn Lys Ala Gly Ile His Thr Asn
            20                  25                  30

Ala Val Tyr Gly Phe Ala Met Leu Leu Glu Lys Ile Leu Lys Glu Glu
        35                  40                  45

Lys Pro Asn His Phe Leu Val Ala Phe Asp Ala Gly Lys Thr Thr Phe
    50                  55                  60

Arg His Glu Lys Tyr Ser Glu Tyr Lys Gly Gly Arg Gln Lys Thr Pro
65                  70                  75                  80

Pro Glu Leu Ser Glu Gln Phe Pro Tyr Ile Arg Gln Leu Leu Asp Ala
                85                  90                  95

Tyr His Ile Lys Arg Tyr Glu Leu Asp Asn Tyr Glu Ala Asp Asp Ile
            100                 105                 110

Ile Gly Thr Leu Ser Lys Glu Ala Asp Lys Ala Gly Phe Gln Thr Ile
        115                 120                 125

Ile Ile Thr Gly Asp Arg Asp Leu Thr Gln Leu Ala Thr Asp Asn Val
    130                 135                 140

Thr Ile Tyr Tyr Thr Lys Lys Gly Val Thr Asp Val Asp His Tyr Thr
145                 150                 155                 160

Pro Asp Phe Ile Ala Glu Lys Tyr Asn Gly Leu Thr Pro Asn Gln Ile
                165                 170                 175
```

```
Ile Asp Met Lys Gly Leu Met Gly Asp Thr Ser Asp Asn Ile Pro Gly
            180                 185                 190

Val Ala Gly Val Gly Glu Lys Thr Ala Ile Lys Leu Leu Asn Gln Phe
            195                 200                 205

Asp Thr Val Glu Gly Val Tyr Glu His Leu Asp Glu Ile Ser Gly Lys
            210                 215                 220

Lys Leu Lys Glu Lys Leu Gln Asn Ser Lys Glu Asp Ala Leu Met Ser
225                 230                 235                 240

Lys Glu Leu Ala Thr Ile Asn Val Asp Ser Pro Ile Glu Val Lys Leu
            245                 250                 255

Glu Asp Thr Leu Met Thr His Gln Asp Glu Gln Gln Lys Ile Glu
            260                 265                 270

Leu Phe Lys Lys Leu Glu Phe Lys Gln Leu Leu Ala Asp Ile Asp Gln
            275                 280                 285

Ser Ala Ser Val Glu Asp Ala Ile Glu Lys Thr Ile Glu Ile Glu Thr
            290                 295                 300

Ser Phe Asp Asn Val Asp Phe Thr Ser Leu Lys Glu Ala Ala Ile His
305                 310                 315                 320

Phe Glu Leu Asp Gly Gly Asn Tyr Leu Arg Asn Asn Ile Leu Lys Phe
            325                 330                 335

Ser Leu Phe Thr Gly Glu Lys His Ile Val Ile Asn Ala Asp Asp Ile
            340                 345                 350

Asn Asn Tyr Ala Glu Leu Val Ser Trp Leu Glu Asn Pro Asn Thr Lys
            355                 360                 365

Lys Val Val Tyr Asp Ala Lys Lys Thr Tyr Val Ala Ser His Arg Leu
            370                 375                 380

Gly Ile Asp Ile Gln Asn Ile Ser Phe Asp Ile Met Leu Ala Ser Tyr
385                 390                 395                 400

Ile Ile Asp Pro Ser Arg Thr Ile Ser Asp Val Gln Ser Val Val Ser
            405                 410                 415

Leu Tyr Gly Gln Ser Phe Val Lys Asp Asp Val Ser Ile Tyr Gly Lys
            420                 425                 430

Gly Lys Lys Phe Lys Val Pro Glu Asp Val Leu Asn Pro Tyr Val
            435                 440                 445

Ala Ser Ile Thr Asp Ala Ile Tyr Phe Ala Lys Pro Asn Met Asp Lys
450                 455                 460

Gln Leu Glu Glu Tyr Asn Gln Val Glu Leu Leu Ala Asp Leu Glu Leu
465                 470                 475                 480

Pro Leu Ala Lys Ile Leu Ser Glu Met Glu Ile Gly Ile Phe Thr
            485                 490                 495

Asp Val His Asp Leu Glu Glu Met Glu Lys Glu Ile Gln Glu Lys Leu
            500                 505                 510

Asp Val Leu Ile Arg Asn Ile His Asp Ala Ala Gly Ser Trp Tyr Gln
            515                 520                 525

Pro Lys Gly Gly Thr Glu Met Phe Cys His Pro Arg Thr Gly Lys Pro
530                 535                 540

Leu Pro Lys Tyr Pro Arg Ile Lys Thr Pro Lys Val Gly Gly Ile Phe
545                 550                 555                 560

Lys Lys Pro Lys Asn Lys Ala Gln Arg Glu Gly Arg Glu Pro Cys Glu
            565                 570                 575

Leu Asp Thr Arg Glu Tyr Val Ala Gly Ala Pro Tyr Thr Pro Val Glu
            580                 585                 590
```

His Val Val Phe Asn Pro Ser Pro Lys Gln Leu Gly Val Val Leu
    595                 600                 605

Phe Glu Thr Leu Gln Leu Pro Val Ile Lys Lys Thr Lys Thr Gly Tyr
610                 615                 620

Ser Thr Ala Val Asp Val Leu Glu Gln Leu Gln Gly Glu His Pro Ile
625                 630                 635                 640

Ile Asp Tyr Ile Leu Glu Tyr Arg Gln Leu Ser Lys Leu Gln Ser Thr
                645                 650                 655

Tyr Val Glu Gly Leu Gln Lys Val Ile Ser Asp Gln Arg Ile His
                660                 665                 670

Thr Arg Phe Asn Gln Thr Leu Ala Gln Thr Gly Arg Leu Ser Ser Val
                675                 680                 685

Asp Pro Asn Leu Gln Asn Ile Pro Val Arg Leu Glu Glu Gly Arg Lys
                690                 695                 700

Ile Arg Lys Ala Phe Lys Pro Thr Ser Lys Asp Ser Val Ile Leu Ser
705                 710                 715                 720

Ala Asp Tyr Ser Gln Ile Glu Leu Arg Val Leu Ala His Ile Thr Gln
                725                 730                 735

Asp Glu Ser Met Lys Glu Ala Phe Ile Asn Gly Asp Asp Ile His Thr
                740                 745                 750

Ala Thr Ala Met Lys Val Phe Gly Val Glu Ala Asp Gln Val Asp Ser
                755                 760                 765

Leu Met Arg Arg Gln Ala Lys Ala Val Asn Phe Gly Ile Val Tyr Gly
                770                 775                 780

Ile Ser Asp Tyr Gly Leu Ser Gln Ser Leu Gly Ile Thr Arg Lys Lys
785                 790                 795                 800

Ala Lys Ala Phe Ile Asp Asp Tyr Leu Ala Ser Phe Pro Gly Val Lys
                805                 810                 815

Gln Tyr Met Ser Asp Ile Val Lys Asp Ala Lys Ala Leu Gly Tyr Val
                820                 825                 830

Glu Thr Leu Leu His Arg Arg Arg Tyr Ile Pro Asp Ile Thr Ser Arg
                835                 840                 845

Asn Phe Asn Leu Arg Gly Phe Ala Glu Arg Thr Ala Met Asn Thr Pro
850                 855                 860

Ile Gln Gly Ser Ala Ala Asp Ile Ile Lys Leu Ala Met Val Lys Phe
865                 870                 875                 880

Ala Gln Lys Met Lys Glu Thr Thr Tyr Gln Ala Lys Leu Leu Leu Gln
                885                 890                 895

Val His Asp Glu Leu Ile Phe Glu Val Pro Lys Ser Gly Val Asp Ser
                900                 905                 910

Phe Ser Glu Phe Val Glu Glu Ile Met Glu Asn Ala Leu Gln Leu Asp
                915                 920                 925

Val Pro Leu Lys Val Asp Ser Ser Tyr Gly Ala Thr Trp Tyr Asp Ala
                930                 935                 940

Lys
945

<210> SEQ ID NO 3
<211> LENGTH: 250
<212> TYPE: DNA
<213> ORGANISM: Artificial Sequence
<220> FEATURE:
<223> OTHER INFORMATION: TBD fragment

<400> SEQUENCE: 3

```
attgaccgaa acgttcggct cgtggtatca gcctaaaggt ggcactgaga tgttctgcca    60
tccgcgaaca ggtaagccac tacctaaata ccctcgcatt aagacaccta aagttggtgg   120
tatctttaag aagcctaaga acaaggcaca gcgagaaggc cgtgagcctt gcgaacttga   180
tacccgcgag tacgttgctg gtgctcctta caccccagtt gaacatgttg tgtttaaccc   240
ttcgtctcgt                                                          250
```

```
<210> SEQ ID NO 4
<211> LENGTH: 46
<212> TYPE: DNA
<213> ORGANISM: Artificial Sequence
<220> FEATURE:
<223> OTHER INFORMATION: PT1_F: upstream primer for amplifying PT1
      fragment of gene Sau

<400> SEQUENCE: 4
catgccatgg aacatcatca tcatcatcat tcagcaagcg ttgaag              46
```

```
<210> SEQ ID NO 5
<211> LENGTH: 28
<212> TYPE: DNA
<213> ORGANISM: Artificial Sequence
<220> FEATURE:
<223> OTHER INFORMATION: PT1_R: downstream primer for amplifying PT1
      fragment of gene Sau

<400> SEQUENCE: 5
gataccacga accagctgca tcatggat                                  28
```

```
<210> SEQ ID NO 6
<211> LENGTH: 37
<212> TYPE: DNA
<213> ORGANISM: Artificial Sequence
<220> FEATURE:
<223> OTHER INFORMATION: PT2_F: upstream primer for amplifying PT2 of
      gene Sau

<400> SEQUENCE: 6
gttgtgttta acccttcgtc tcctaagcaa ttaggtg                        37
```

```
<210> SEQ ID NO 7
<211> LENGTH: 26
<212> TYPE: DNA
<213> ORGANISM: Artificial Sequence
<220> FEATURE:
<223> OTHER INFORMATION: PT2_R: downstream primer for amplifying PT2
      fragment of gene Sau

<400> SEQUENCE: 7
cgcggatcct tattttgcat catacc                                    26
```

```
<210> SEQ ID NO 8
<211> LENGTH: 30
<212> TYPE: DNA
<213> ORGANISM: Artificial Sequence
<220> FEATURE:
<223> OTHER INFORMATION: TBD_F: upperstream primer for amplifying TBD
      fragment

<400> SEQUENCE: 8
tgcagctggt tcgtggtatc agcctaaagg                                30
```

```
<210> SEQ ID NO 9
<211> LENGTH: 37
<212> TYPE: DNA
```

```
<213> ORGANISM: Artificial Sequence
<220> FEATURE:
<223> OTHER INFORMATION: Downstream primer for amplifying TBD fragment

<400> SEQUENCE: 9
cacctaattg cttaggagac gaagggttaa acacaac                               37

<210> SEQ ID NO 10
<211> LENGTH: 33
<212> TYPE: DNA
<213> ORGANISM: Artificial Sequence
<220> FEATURE:
<223> OTHER INFORMATION: Trx_F: upstream primer for amplifying gene TrxA

<400> SEQUENCE: 10
catgccatgg gcagcgataa aattattcac ctg                                   33

<210> SEQ ID NO 11
<211> LENGTH: 37
<212> TYPE: DNA
<213> ORGANISM: Artificial Sequence
<220> FEATURE:
<223> OTHER INFORMATION: Trx_R: downstream primer for amplifying gene
      TrxA

<400> SEQUENCE: 11
ttttcctttt gcggccgccg ccaggttagc gtcgagg                               37

<210> SEQ ID NO 12
<211> LENGTH: 18
<212> TYPE: DNA
<213> ORGANISM: Artificial Sequence
<220> FEATURE:
<223> OTHER INFORMATION: M13-40: testing primer M13-40

<400> SEQUENCE: 12
gttttcccag tcacgacg                                                    18

<210> SEQ ID NO 13
<211> LENGTH: 34
<212> TYPE: DNA
<213> ORGANISM: Artificial Sequence
<220> FEATURE:
<223> OTHER INFORMATION: M13-40LF: testing primer M13-40LF

<400> SEQUENCE: 13
gttttcccag tcacgacgtt gtaaaacgac ggcc                                  34

<210> SEQ ID NO 14
<211> LENGTH: 30
<212> TYPE: DNA
<213> ORGANISM: Artificial Sequence
<220> FEATURE:
<223> OTHER INFORMATION: 500_F: testing primer 500_F

<400> SEQUENCE: 14
actactaaat cctgaatagc tttaagaagg                                       30

<210> SEQ ID NO 15
<211> LENGTH: 30
<212> TYPE: DNA
```

```
<213> ORGANISM: Artificial Sequence
<220> FEATURE:
<223> OTHER INFORMATION: 500_R: testing primer 500_R

<400> SEQUENCE: 15
cagaaagcta aatatggaaa actacaatac                                            30
```